United States Patent [19]
Pierson, III

[11] Patent Number: 6,042,584
[45] Date of Patent: Mar. 28, 2000

[54] BONE DEPTH RESECTION GUIDE AND METHOD

[76] Inventor: Raymond H. Pierson, III, 62 W. Columbia St., Suite C, Orlando, Fla. 32806

[21] Appl. No.: 09/205,593

[22] Filed: Dec. 4, 1998

[51] Int. Cl.⁷ .................................................. A61B 17/58
[52] U.S. Cl. ............................. 606/102; 606/73; 606/77; 411/5
[58] Field of Search .................... 606/72, 73, 75, 606/76, 77, 102, 116, 117; 411/2, 3, 4, 5

[56] References Cited

U.S. PATENT DOCUMENTS

| | | |
|---|---|---|
| 3,343,443 | 9/1967 | Moore ........................................ 411/3 |
| 3,915,162 | 10/1975 | Miller ...................................... 606/73 |
| 4,005,527 | 2/1977 | Wilson et al. . |
| 4,421,112 | 12/1983 | Mains et al. . |
| 4,815,467 | 3/1989 | Chestnut . |
| 4,978,351 | 12/1990 | Rozas . |
| 5,129,904 | 7/1992 | Illi ............................................ 606/72 |
| 5,129,906 | 7/1992 | Ross et al. ............................... 606/77 |
| 5,169,400 | 12/1992 | Muhling et al. ......................... 606/73 |
| 5,562,704 | 10/1996 | Tamminmaki et al. ................. 606/75 |
| 5,895,396 | 4/1999 | Day et al. ................................ 606/72 |

*Primary Examiner*—Michael Buiz
*Assistant Examiner*—Julian W. Woo
*Attorney, Agent, or Firm*—Allen, Dyer, Doppelt, Milbrath & Gilchrist, P.A.

[57] ABSTRACT

A gauge for measuring bone thickness includes an elongated pin for insertion into a bore through a bone section. The pin has a length sufficient to span the entire bone section with a distal tip protruding therefrom. The pin further has a length measurement indicator disposed along an outer surface, such as a series of colored bands or indicia, the visualization of which communicates bone thickness. The gauge also has a head at a proximal end of the pin, which is dimensioned to prevent its movement into the bone section's bore. In a particular embodiment a protrusion extending away from the pin's outer surface is provided to retain the pin within the bore. Methods are also described for measuring bone thickness and for contouring bone.

35 Claims, 4 Drawing Sheets

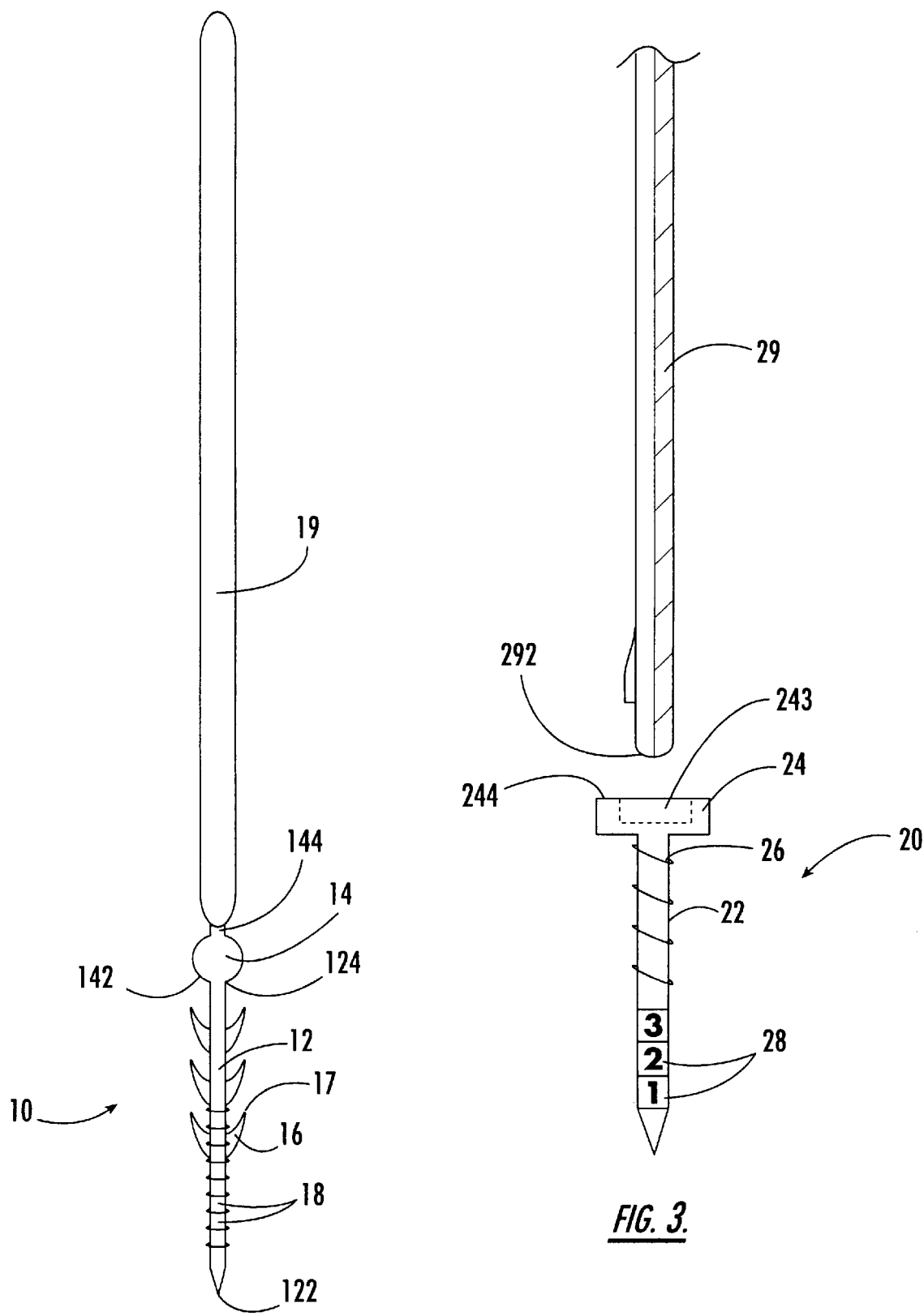

BONE DEPTH RESECTION GUIDE AND METHOD

BACKGROUND OF THE INVENTION

1. Field of the Invention

The present invention relates to devices and methods for resectioning a bone, and, more particularly, to devices and associated methods for gauging resection depth.

2. Description of Related Art

In arthroscopic surgical procedures for alleviating joint damage, it is typical to remove a portion of a bone. An exemplary procedure is that undertaken to correct impingement syndrome in the shoulder, when the subacromial space in the rotator cuff is tight, or if a spur or downward curvature is present in the acromion. Bone may also be thinned preparatory to attaching a soft tissue graft, such as in anterior cruciate ligament replacement surgery, wherein 5–7 mm of the lateral femoral condyle may be removed to perform attachment.

At present there is no known method of determining precisely how much bone should be removed, nor of gauging how much bone has been removed during the procedure. As these procedures are performed through the limited perspective available from arthroscopy, further limited by its monocular nature, depth perception is compromised. Consequently, a surgeon may remove an insufficient amount of bone, possibly mis-sizing the impingement problem, or may oversize, creating an inadequate fit, potentially leaving the patient with too little bone mass and with a susceptibility to subsequent fracture.

Other situations also require a knowledge of bone thickness: for gauging bone removal in an osteomyelitis procedure, during reaming of long bones having intramedullary fractures, and for cortex thinning prior to insertion of stemmed arthroplasty components. There is currently no device or method for measuring bone thickness for any of these applications.

SUMMARY OF THE INVENTION

It is therefore an object of the present invention to provide a device for gauging bone thickness during a surgical procedure.

It is an additional object to provide such a device for use in arthroscopic procedures.

It is a further object to provide such a device that is biocompatible.

It is another object to provide such a device that is bioresorbable.

It is yet an additional object to provide such a device that provides a continuous indication of bone thickness.

It is yet a further object to provide a system for measuring a bone shape.

It is yet another object to provide a system for contouring a bone to a desired shape.

An additional object is to provide a method of gauging bone thickness during a surgical procedure.

A further object is to provide a method of deploying a bone thickness gauge during a surgical procedure.

Another object is to provide a method for contouring a bone to a predetermined shape.

Yet an additional object is to provide a method of defining an anatomical boundary for an arthroscopic procedure.

These objects and others are attained by the present invention, a bone depth gauge and methods of using. The gauge, which is for measuring bone thickness, includes an elongated pin for insertion into a bore through a bone section slated for resection. The pin has a length sufficient to span the entire bone section with a distal tip protruding therefrom. Additionally, the pin comprises a material that is excisable along with the bone material.

The pin further has a length measurement indicator disposed along at least a portion of an outer surface, such as, but not limited to, a series of colored bands or indicia, the visualization of which communicates bone thickness.

The gauge also has a head affixed at a proximal end of the pin, and preferably coformed therewith, which is dimensioned to prevent its movement into the bone section's bore. In a particular embodiment a protrusion, such as a barb or screw thread, extends from the pin's outer surface to assist in retaining the pin within the bore.

Methods utilizing such a gauge are valuable in arthroscopic procedures, for example, in resectioning an anterior corner of an acromion to relieve effects of tight tolerances in the rotator cuff area of the shoulder. Another exemplary use is in notchplasty, such as in the removal of bone material from the medial wall of the lateral femoral condyle preparatory to anterior cruciate ligament replacement in the knee. Yet another exemplary use is in reaming a bone canal to remove bone and/or cement material.

A further method includes utilizing a plurality of the above-described gauges disposed about a section of bone to permit the contouring of the bone to a predetermined shape, with each gauge being visualized to ascertain a bone thickness at a plurality of points about the bone section.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side perspective view of a bone thickness gauge.

FIG. 3 is a side perspective view of an alternate embodiment of a bone thickness gauge.

DETAILED DESCRIPTION OF THE PREFERRED EMBODIMENTS

A description of the preferred embodiments of the present invention will now be presented with reference to FIGS. 1–8.

Figure 2:
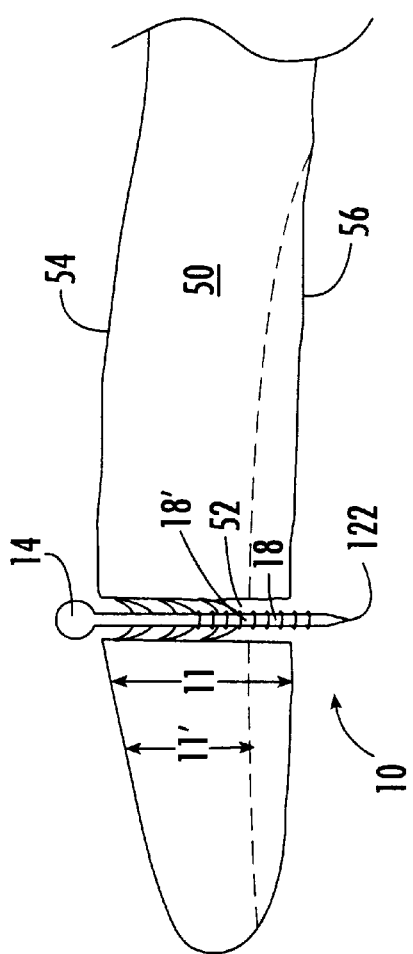
FIG. 2 is a side cross-sectional view of the bone thickness gauge inserted into a bone for use in depth resection.

A first embodiment of the bone depth gauge 10 for measuring bone thickness is illustrated in FIGS. 1 and 2. Preferably the gauges of the present invention comprise a biocompatible material; more preferably, the gauges comprise a bioresorbable material. In another embodiment the gauge comprises a porous, biocompatible material adapted to encourage bone regrowth therearound and thereinto. The gauge 10 comprises an elongated pin 12 dimensioned to be inserted through a bore 52 in a section of bone 50. The pin 12 is sufficiently long that its distal tip 122, typically pointed, protrudes from the bone's distal face 56.

Figure 8:
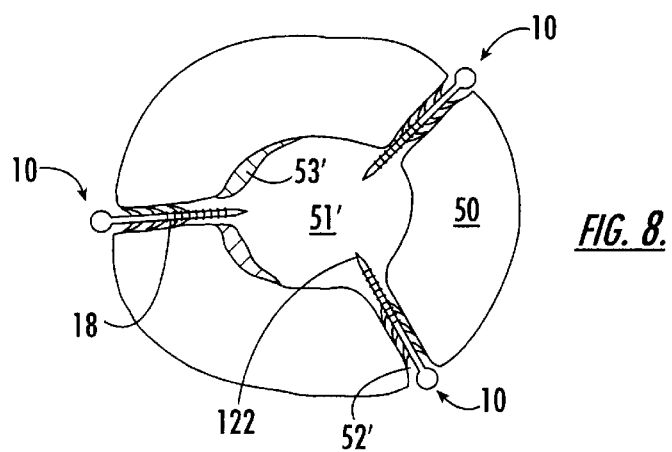
FIG. 8 is an axial cross-sectional view of a plurality of bone thickness gauges inserted into a bone canal preparatory to reaming the canal.

In another related embodiment the pin 12 is dimensioned to be inserted through a bore 52' into a bone canal 51' of a bone 50' (see FIG. 8).

In a preferred embodiment the pin's outer surface comprises means for resisting removal of the pin 12 from the bone section's bore 52. Such means may comprise, for example, barbs 16 disposed along the outer surface, the barbs having tips 17 directed in a generally proximal direction, so that, once inserted, the barbs 16 resist a pulling force out of the bore 52.

A head 14 is affixed at the pin's proximal end 124, and is dimensioned to prevent its movement into the bone bore 52 from the bone's proximal face 54. Preferably the head 14 has a shape expanding outward from its distal end 142, such as a flared shape, which serves to minimize measurement errors caused by misalignment, although this is not intended as a limitation. The head may also comprise, for example, a round or parabolic shape.

In one embodiment of the invention, in order to facilitate insertion, the head's proximal end 144 is frangibly affixed to an elongated drive member 19, which is generally coaxial with the pin 12 and extends in a proximal direction. In use, the drive member 19 is used to insert the gauge 10 into the bone bore 52, and, when the head 14 contacts the bone's proximal face 54, is broken off and discarded. The drive member 19 is typically preferred since soft tissue may need to be traversed before reaching bone.

In other embodiments the head's proximal end 144 may comprise a noncircular depression for being driven with a commensurately shaped driver, such as a hexagonal-shaped depression for being driven with a hex driver. Alternatively, the gauge 10 may be driven by a device such as a staple gun.

Means are provided on the outer surface of the pin 12 for indicating a length measurement along the pin's longitudinal axis. Such an indicator may comprise, for example, a plurality of successive distinctive, generally circumferential, bands 18, such as bands 18 having different colors, as in a rainbow progression. For this embodiment, the user is provided with a color chart against which to compare a colored band with a depth value.

In use, then, the surgeon would visualize the protruding distal tip 122 of the pin 12 and note the color of the band 18 closest to the bone's distal face 56. Typically the protruding distal tip 122 will be excised in order to avoid losing a piece of pin 12 during bone material removal. Knowing precisely the thickness 11 of the bone 50 at this point, the surgeon could then determine to remove bone material and pin material until a desired thickness 11' is reached, at which point a band 18' of a different color would be visible (shown as a dashed line in FIG. 2). With this device and method, it can be seen that the surgeon is permitted to resection the bone 50 to a predetermined desired thickness.

Figure 4:
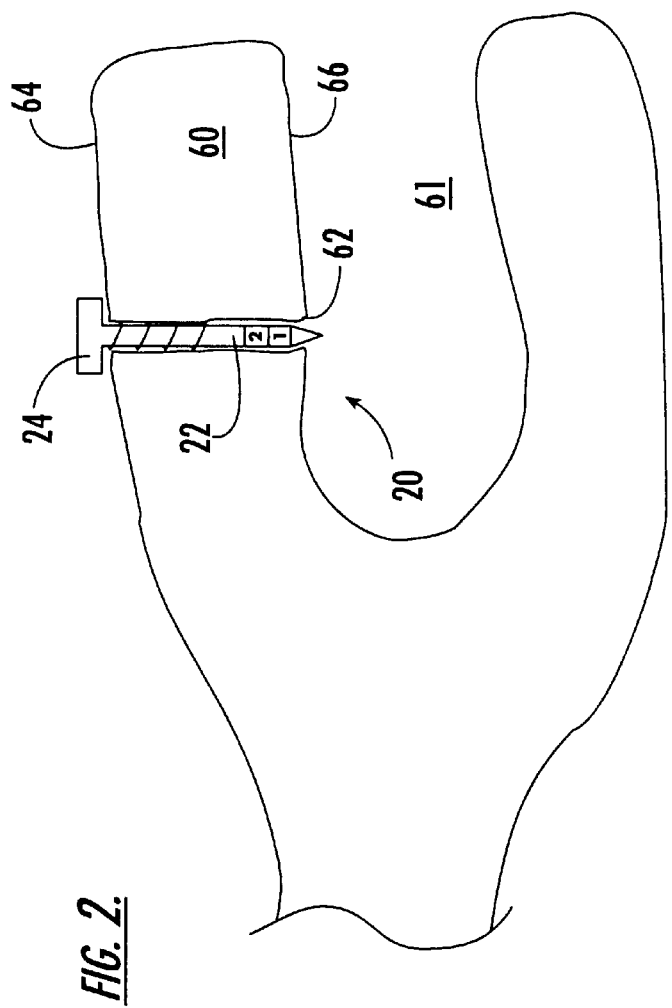
FIG. 4 is a side cross-sectional view of the bone thickness gauge inserted for use in notchplasty.

In a second embodiment, illustrated in FIGS. 3 and 4, the bone depth gauge 20 has a pin 22 similar to that described above, except that the means for resisting removal comprises a screw-type thread 26 disposed along at least a portion of the pin's outer surface. In this case the drive member 29 would permit a screwing-type motion for insertion, such as into a bore 62 into a femoral condyle 60 from a proximal face 64 through to a distal face 66 into the notch 61. The bone depth gauge 20 also has a head 24, here a flat head 24, with a hex-shaped depression 243 in the head's proximal face 244. Such a gauge 20 is then drivable with a screwdriver-type device 29 having a commensurately shaped distal end 292 for insertion into the depression 243.

The indicator means in this embodiment comprises a plurality of successive indicia disposed along the pin 22, for example, a series of numbers 28.

Figure 5:
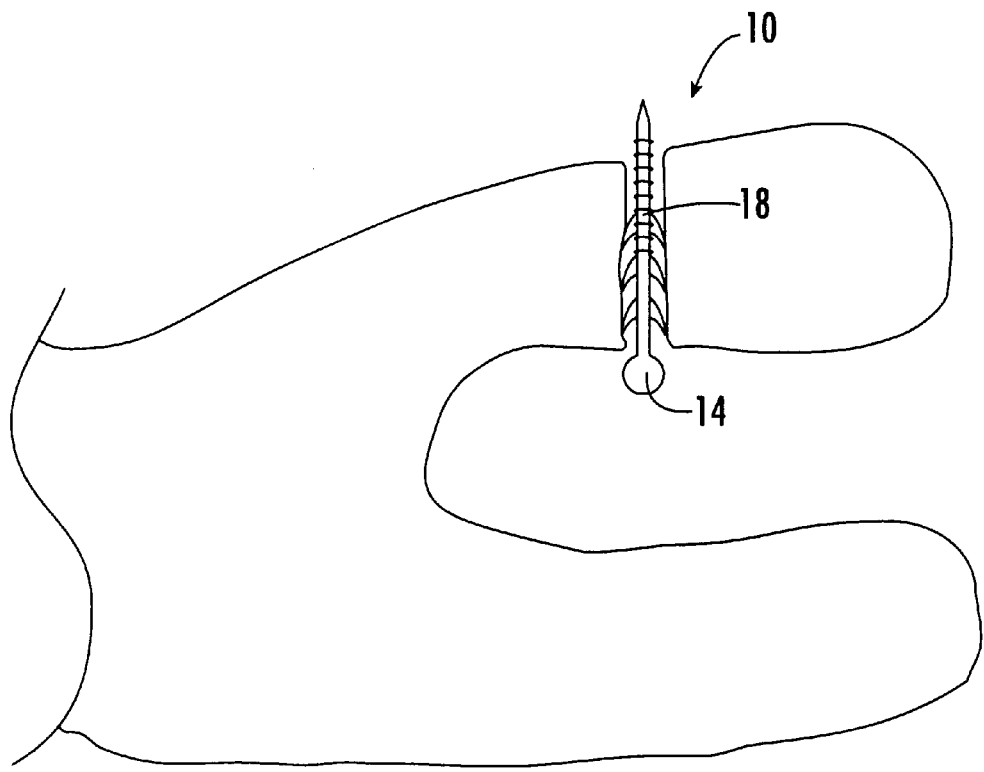
FIG. 5 is a side cross-sectional view of the bone thickness gauge of FIG. 1 inserted for use in notchplasty, with resectioning beginning from the gauge's head region.

In a third embodiment, either of the above gauge embodiments 10 or 20 can be resected from the opposite end. As illustrated in FIG. 5 for gauge 10, it may be more convenient in some procedures to insert a gauge 10 so that the head 14 is located at the desired bone-removal site. In this case, then, the indicia bands 18 are visualized starting from the head 14, with the surgeon referring to a chart that is the inverse of that described above to read off a resection depth value. This embodiment permits, for example, a resectioning of an acromion from the bottom, without requiring an additional portal.

Figure 6:
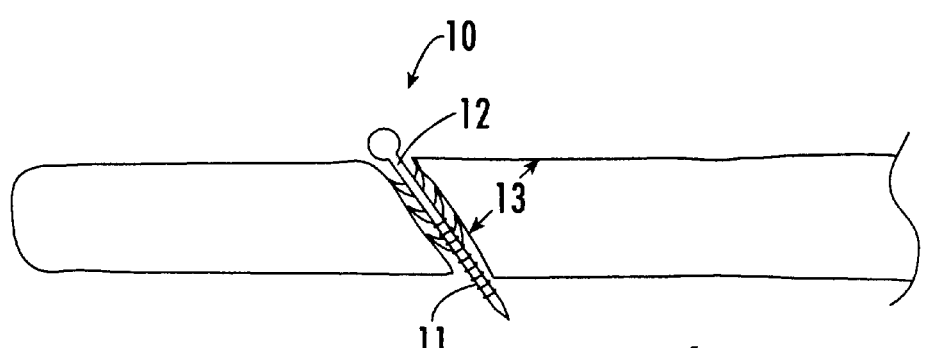
FIG. 6 is a side cross-sectional view of a radio-opaque bone-thickness gauge inserted at an angle to the bone face.

In a fourth embodiment, a gauge comprises radio-opaque material so that it may be visualized radiographically following insertion. As illustrated in FIG. 6 for gauge 10 with a radio-opaque coating 11, insertion may not always proceed normal to the bone surface, which may or may not be intentional. The ability to noninvasively visualize the angle 13 described by the pin 12 section, however, still provides the surgeon with sufficient information to determine resection depth. A trigonometric chart would be provided so that the surgeon could, knowing the angle 13, determine how the indicia bands 18 correlate with a depth perpendicular to the bone surface.

Figure 7:
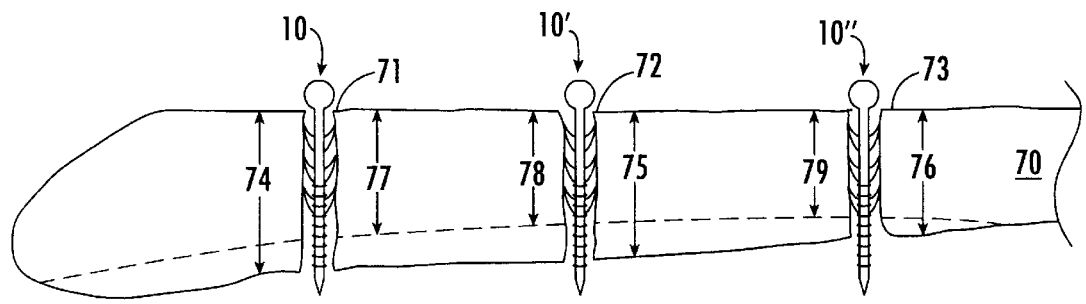
FIG. 7 is a side cross-sectional view of a plurality of bone thickness gauges inserted into a bone for use in contouring a bone.

While one gauge 10,20 may be used to indicate a bone thickness at a particular location, and to provide a continual readout during resectioning, a surgeon may also perform a relatively precise bone contouring procedure with the use of a plurality of gauges, as shown in FIG. 7 for gauges 10. Typically one or more images of the target bone 70 will have been taken prior to the procedure, and the surgeon will have determined a desired bone shape (illustrated as a dashed line in FIG. 7) and a map therefor.

In this method a plurality of gauges, here three gauges 10,10',10" are inserted in three bores 71,72,73 in the bone 70. Owing to the elasticity of the skin and underlying soft tissue, typically a plurality of gauges can be placed through a unitary skin incision, which is a significant benefit. Thicknesses 74,75,76 are determined with the use of the gauges 10,10',10". Resectioning and concomitant pin excision are carried out in stages, such as with a burr or any device known in the art, periodically visualizing the gauges 10,10', 10" to determine current thickness values. This procedure is repeated until the desired thicknesses 77,78,79 at each location are achieved.

Insertion of the gauges 10,20 may be accomplished in a number of ways. In a particular embodiment, a bore is drilled through the bone section and a gauge is inserted thereinto. In another embodiment, a driver is utilized that has elements for creating the bore in one step, such as with a drill having a stop, and then driving the gauge into the bore in another step. Such a device would likely only require a single puncture wound in the patient's skin to deploy a desired number of gauges owing to the skin's elasticity.

Alternatively, a device such as a staple gun could be used, as mentioned above, which could be cannulated.

In yet another embodiment, illustrated in FIG. 8, the gauge 10 can be used to aid in reaming a canal 51' in a bone 50' of bone material and/or cement 53' from an implant. In this case the method includes inserting a gauge 10, preferably a plurality of gauges 10, through bore(s) 52' drilled in the bone 50' into the canal 51' and visualizing a distal tip 122 of each gauge 10 protruding into the bone canal 51'. Next a distal portion of the gauges 10 and a portion of bone and/or cement are removed from the canal 51'. As above, it is then determined from the bands 18 how much of the bone and/or cement material has been removed. These steps are then repeated until a predetermined desired amount of bone and/or cement material has been removed.

This method has a number of benefits over previously known surgical techniques: When it is desired to remove only cement from a canal, it is often difficult to differentiate between cement and bone material, and removal of bone stock may be excessive, or a bone may even be perforated, especially in curving bones. This method prevents these problems, and permits retaining a predetermined thickness of bone cortex. This method can also be used to prepare the bone for a cementless implant.

It may be appreciated by one skilled in the art that additional embodiments may be contemplated, including gauges having alternate shapes and indicator means.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A bone depth gauge comprising:
   an elongated pin for insertion into a bore through a bone section to be resected, the pin having a length sufficient to span the entire bone section with a distal tip protruding therefrom and further having a plurality of successive, different-colored generally circumferential bands disposed along at least of portion of an outer surface for indicating a length measurement therealong, the pin comprising a material excisable with bone material; and
   a head affixed at a proximal end of the pin dimensioned to prevent a movement thereof into the bone section bore.

2. The bone depth gauge recited in claim 1, wherein the bands are generally circumferentially disposed along at least a distal portion of the pin.

3. The bone depth gauge recited in claim 1, wherein the bands are generally circumferentially disposed along at least a proximal portion of the pin.

4. The bone depth gauge recited in claim 1, wherein the pin distal tip is pointed to facilitate insertion through the bone section bore.

5. The bone depth gauge recited in claim 1, wherein the head has a generally flared shape from a distal end for minimizing measurement error owing to a potential misalignment during insertion.

6. The bone depth gauge recited in claim 1, wherein the head shape comprises a smoothly increasing contour from a distal end for minimizing measurement error owing to a potential misalignment during insertion.

7. The bone depth gauge recited in claim 1, wherein the pin and the head comprise a biocompatible material.

8. The bone depth gauge recited in claim 1, wherein the pin and the head comprise a bioresorbable material.

9. The bone depth gauge recited in claim 1, wherein the pin has an appearance sufficiently distinguishable from bone and cement to permit in situ visualization thereof.

10. The bone depth gauge recited in claim 1, wherein the pin and the head comprise a porous, bioresorbable material adapted to encourage bone regrowth therearound and thereinto.

11. The bone depth gauge recited in claim 1, wherein the pin further has means for resisting removal from the bone section bore.

12. The bone depth gauge recited in claim 1, wherein the head comprises means for being driven by an elongated drive member.

13. A bone depth gauge comprising:
   an elongated pin for insertion into a bore through a bone section to be resected, the pin having a length sufficient to span the entire bone section with a distal tip protruding therefrom and further having a plurality of successive, different-colored generally circumferential bands having successive indicia disposed along at least of portion of an outer surface for indicating a length measurement therealong, the pin comprising a material excisable with bone material; and
   a head affixed at a proximal end of the pin dimensioned to prevent a movement thereof into the bone section bore.

14. The bone depth gauge recited in claim 13, wherein the indicia comprise numbers.

15. A bone depth gauge comprising:
   an elongated pin for insertion into a bore through a bone section to be resected, the pin having a length sufficient to span the entire bone section with a distal tip protruding therefrom and further having a plurality of successive, mutually distinguishable generally circumferential bands disposed along at least of portion of an outer surface for indicating a length measurement therealong, the bands selected from a group consisting of different-colored bands and bands having successive indicia disposed thereon, the pin comprising a material excisable with bone material, the pin further having a screw-type thread disposed along at least a portion of the outer surface for resisting removal from the bone section bore; and
   a head affixed at a proximal end of the pin dimensioned to prevent a movement thereof into the bone section bore.

16. A bone depth gauge comprising:
   an elongated pin for insertion into a bore through a bone section to be resected, the pin having a length sufficient to span the entire bone section with a distal tip protruding therefrom and further having a plurality of successive, mutually distinguishable generally circumferential bands disposed along at least of portion of an outer surface for indicating a length measurement therealong, the bands selected from a group consisting of different-colored bands and bands having successive indicia disposed thereon, the pin comprising a material excisable with bone material, the pin further having a plurality of barbs disposed along the outer surface and having tips directed generally proximally for resisting removal from the bone section bore; and a head affixed at a proximal end of the pin dimensioned to prevent a movement thereof into the bone section bore.

17. A bone depth gauge comprising:

an elongated pin for insertion into a bore through a bone section to be resected, the pin having a length sufficient to span the entire bone section with a distal tip protruding therefrom and further having a plurality of successive, mutually distinguishable generally circumferential bands disposed along at least a portion of an outer surface for indicating a length measurement therealong, the bands selected from a group consisting of different-colored bands and bands having successive indicia disposed thereon, the pin comprising a material excisable with bone material;

a head affixed at a proximal end of the pin dimensioned to prevent a movement thereof into the bone section bore; and an elongated drive member frangibly affixed to the head and extending proximally generally coaxially with the pin, for facilitating insertion.

18. A bone depth gauge comprising:

an elongated pin for insertion into a bore through a bone section to be resected, the pin having a length sufficient to span the entire bone section with a distal tip protruding therefrom and further having a plurality of successive, mutually distinguishable generally circumferential bands disposed along at least of portion of an outer surface for indicating a length measurement therealong, the bands selected from a group consisting of different-colored bands and bands having successive indicia disposed thereon, the pin comprising a material excisable with bone material; and a head affixed at a proximal end of the pin dimensioned to prevent a movement thereof into the bone section bore, the head having a depression that is noncircular in axial cross section in a proximal face thereof for being driven by a drive member having a commensurately shaped protrusion at a distal end.

19. A bone depth measurement system comprising:

a bone depth gauge comprising:

an elongated pin for insertion into a bore through a bone section to be resected, the pin having a length sufficient to span the entire bone section with a distal tip protruding therefrom and further having a plurality of mutually distinguishable bands on an outer surface for indicating a length measurement therealong, the bands selected from a group consisting of different-colored bands and bands having successive indicia disposed theron, the pin comprising a material excisable with bone material; and a head at a proximal end of the pin dimensioned to prevent a movement thereof into the bone section bore; and means for inserting the gauge through the bone section.

20. The bone depth measurement system recited in claim 19, wherein the inserting means comprises means for inserting the gauge through a hole made through the bone section.

21. The bone depth measurement system recited in claim 20, wherein the inserting means comprises an elongated drive member frangibly affixed to the head and extending proximalward generally coaxially with the pin.

22. The bone depth measurement system recited in claim 20, wherein the head comprises means for being driven by an elongated drive member.

23. The bone depth measurement system recited in claim 19, wherein the inserting means comprises a power driver for forcing the gauge through the bone section.

24. The bone depth measurement system recited in claim 19, further comprising reference means for translating the band into a depth measurement.

25. The bone depth measurement system recited in claim 19, wherein the gauge comprises an imagable material for noninvasively ascertaining a position and an angle of the pin relative to a face of the bone section.

26. The bone depth measurement system recited in claim 25, further comprising reference means for translating the bands and pin angle into a bone depth measurement.

27. A bone depth measurement system comprising:

a bone depth gauge comprising:

an elongated pin for insertion into a bore through a bone section to be resected, the pin having a length sufficient to span the entire bone section with a distal tip protruding therefrom and further having a plurality of mutually distinguishable generally circumferential bands disposed on an outer surface for indicating a length measurement therealong, the pin comprising a material excisable with bone material; and a head at a proximal end of the pin dimensioned to prevent a movement thereof into the bone section bore;

means for inserting the gauge through the bone section; and a chart for correlating an appearance of each band with a bone depth measurement.

28. A bone contouring system comprising:

a plurality of bone depth gauges, each comprising:

an elongated pin for insertion into a bore through a bone section to be resected, the pin having a length sufficient to span the entire bone section with a distal tip protruding therefrom and further having a plurality of mutually distinguishable bands on an outer surface for indicating a length measurement therealong, the bands selected from a group consisting of different-colored bands and bands having successive indicia disposed theron, the pin comprising a material excisable with bone material; and a head at a proximal end of the pin dimensioned to prevent a movement thereof into the bone section bore;

means for disposing the gauges about a predetermined region of a bone, for providing a measurement of bone thickness within the bone region; and means for removing bone material within the bone region, the gauges providing a measurement of remaining bone thickness.

29. A method of removing a predetermined amount of bone material comprising the steps of:

inserting a bone depth gauge through a section of bone to be resected, the gauge having an elongated distal pin section having a length greater than a depth of the bone section, a head at a proximal end, and length indicating means along at least a distal portion of the pin;

visualizing a distal tip of the gauge protruding from a distal face of the bone;

removing a distal portion of the gauge and a portion of bone from the distal face;

determining from the indicating means on the gauge newly created distal end an amount of the bone section that has been removed; and repeating the visualizing, removing, and determining steps until a predetermined desired amount of bone material has been removed.

30. A method of removing a predetermined amount of bone material comprising the steps of:

inserting a bone depth gauge through a section of bone to be resected, the gauge having an elongated distal pin section, a head at a proximal end and length indicating means along at least a proximal portion of the pin;

visualizing the gauge head protruding from a proximal face of the bone;

removing a proximal portion of the gauge and a portion of bone from the proximal face;

determining from the indicating means on the gauge newly created proximal end an amount of the bone section that has been removed; and repeating the visualizing, removing, and determining steps until a predetermined desired amount of bone material has been removed.

31. A method for contouring a section of bone comprising the steps of:

inserting a plurality of bone depth gauges through a plurality of locations about a section of bone to be resected, the gauges each having length indicating means on at least a distal section thereof;

visualizing a distal end of each gauge protruding from a distal face of the bone;

determining from the indicating means on each protruding gauge distal end a thickness at each location of the bone section;

removing a portion of the pin along with a portion of bone from the distal face; and repeating the visualizing, determining, and removing steps until the bone section has a desired thickness at each location.

32. The method recited in claim 31, wherein the inserting step comprises making a unitary incision through skin and soft tissue superficial to the bone section and inserting each of the bone depth gauges through the unitary incision.

33. The method recited in claim 31, further comprising the step, prior to the removing step, of cutting off the protruding gauge distal end.

34. A method for reaming a bone canal to remove bone material and/or cement material therefrom, the method comprising the steps of:

inserting a bone thickness gauge through a section of bone having a canal to be reamed, the gauge having an elongated distal pin section having a length greater than a thickness of the bone section from a surface to the canal, a head at a proximal end, and length indicating means along at least a distal portion of the pin;

visualizing a distal tip of the gauge protruding into the bone canal;

reaming a distal portion of the gauge and a portion of bone and/or cement from the canal;

determining from the indicating means on the gauge newly created distal end an amount of the bone and/or cement material that has been removed; and repeating the visualizing, reaming, and determining steps until a predetermined desired amount of bone and/or cement material has been removed.

35. The method recited in claim 34, wherein the inserting step comprises a plurality of gauges through a plurality of bores into the bone canal, the bores disposed circumferentially about the bone surface.

* * * * *